(12) United States Patent
Piller et al.

(10) Patent No.: US 11,051,956 B2
(45) Date of Patent: Jul. 6, 2021

(54) PROSTHESIS COSMETIC ELEMENT, AND SYSTEM CONSISTING OF PROSTHESIS COSMETIC ELEMENT AND PROSTHESIS

(71) Applicant: Otto Bock Healthcare Products GmbH, Vienna (AT)

(72) Inventors: Markus Piller, Vienna (AT); Hans Oppel, Vienna (AT); Sonja Wagner, Vienna (AT); Johannes Bischof, Wiener Neustadt (AT); Alice Frey, Stockerau (AT); Raphael Scheffel, Vienna (AT); Walter Lunzer, Vienna (AT); Mario Koppe, Göttingen (DE); Andreas Leiniger, Leinefelde OT Birkungen (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 63 days.

(21) Appl. No.: 16/339,928

(22) PCT Filed: Sep. 20, 2017

(86) PCT No.: PCT/EP2017/073787
§ 371 (c)(1),
(2) Date: Apr. 5, 2019

(87) PCT Pub. No.: WO2018/065218
PCT Pub. Date: Apr. 12, 2018

(65) Prior Publication Data
US 2020/0038203 A1    Feb. 6, 2020

(30) Foreign Application Priority Data
Oct. 6, 2016    (DE) .................... 10 2016 119 001.2

(51) Int. Cl.
*A61F 2/64* (2006.01)
*A61F 2/58* (2006.01)
(Continued)

(52) U.S. Cl.
CPC ................ *A61F 2/64* (2013.01); *A61F 2/582* (2013.01); *A61F 2/66* (2013.01);
(Continued)

(58) Field of Classification Search
CPC .... A61F 2/64; A61F 2/582; A61F 2/66; A61F 2/604; A61F 2002/5001; A61F 2002/5038; A61F 2002/5083; A61F 2002/6614
See application file for complete search history.

(56) References Cited

U.S. PATENT DOCUMENTS 5,376,127 A    12/1994    Swanson
5,880,964 A    3/1999    Schall et al.
(Continued)

FOREIGN PATENT DOCUMENTS

DE    7635606 U1    9/1977
DE    20309318 U1    9/2003
(Continued)

OTHER PUBLICATIONS

International Search Report for International Application No. PCT/EP2017/073787, dated Dec. 15, 2017, 3 pages.

*Primary Examiner* — Suba Ganesan
*Assistant Examiner* — Aren Patel
(74) *Attorney, Agent, or Firm* — Holland & Hart LLP

(57) ABSTRACT

A prosthesis cosmetic element for a prosthesis comprising a prosthesis joint which has an upper part and a lower part that is mounted thereon in a pivotal manner about a pivot axis, the prosthesis cosmetic element has a first frame part, which has at least one first securing device for fixing on the lower (Continued)

part, and a second frame part with at least one second securing device for securing on the upper part. The frame parts are mounted in a pivotal manner relative to each other, and the prosthesis joint is equipped with a rotational element on which an actuating element is arranged. The actuating element is accessible from the outside by a frame part or through a frame part.

20 Claims, 15 Drawing Sheets

(51) Int. Cl.
*A61F 2/66* (2006.01)
*A61F 2/50* (2006.01)
*A61F 2/60* (2006.01)

(52) U.S. Cl.
CPC ............... *A61F 2002/5001* (2013.01); *A61F 2002/5038* (2013.01); *A61F 2002/5083* (2013.01); *A61F 2002/607* (2013.01); *A61F 2002/6614* (2013.01)

(56) References Cited

U.S. PATENT DOCUMENTS

| | | |
|---|---|---|
| 6,597,965 B2 | 7/2003 | Graves et al. |
| 6,740,124 B1 | 5/2004 | Laghi |
| 8,366,789 B2 | 2/2013 | Summit |
| 2007/0016215 A1 | 1/2007 | Wilander et al. |
| 2007/0150069 A1 | 6/2007 | Takami et al. |
| 2014/0371872 A1* | 12/2014 | Sawatzki .................. A61F 2/50 623/27 |
| 2015/0081038 A1* | 3/2015 | Rauch ....................... A61F 2/60 623/33 |
| 2016/0206447 A1* | 7/2016 | Auberger .................. A61F 2/70 |
| 2016/0331560 A1* | 11/2016 | Tong ...................... A61B 5/112 |

FOREIGN PATENT DOCUMENTS

| | | |
|---|---|---|
| DE | 202007009077 U1 | 11/2007 |
| DE | 102012009757 A1 | 12/2013 |
| DE | 102014015756 B3 | 2/2016 |
| WO | 2010054341 A1 | 5/2010 |

* cited by examiner

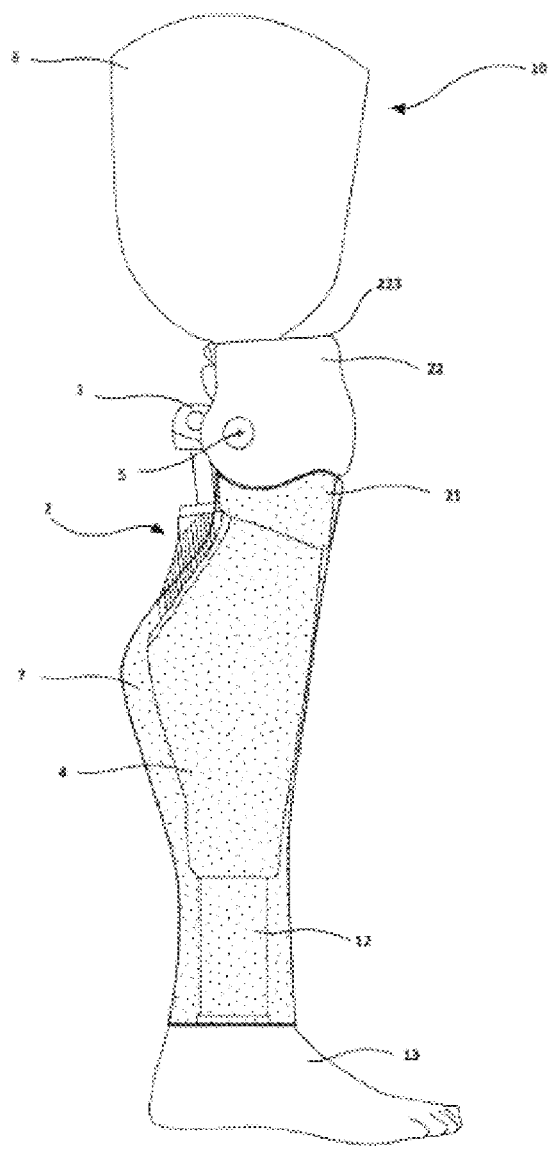

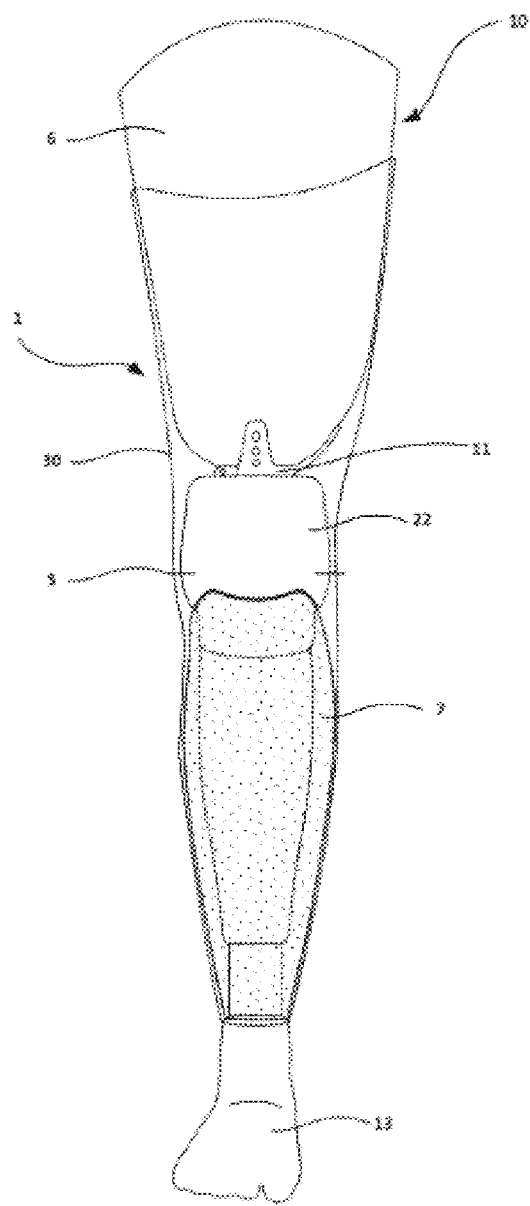

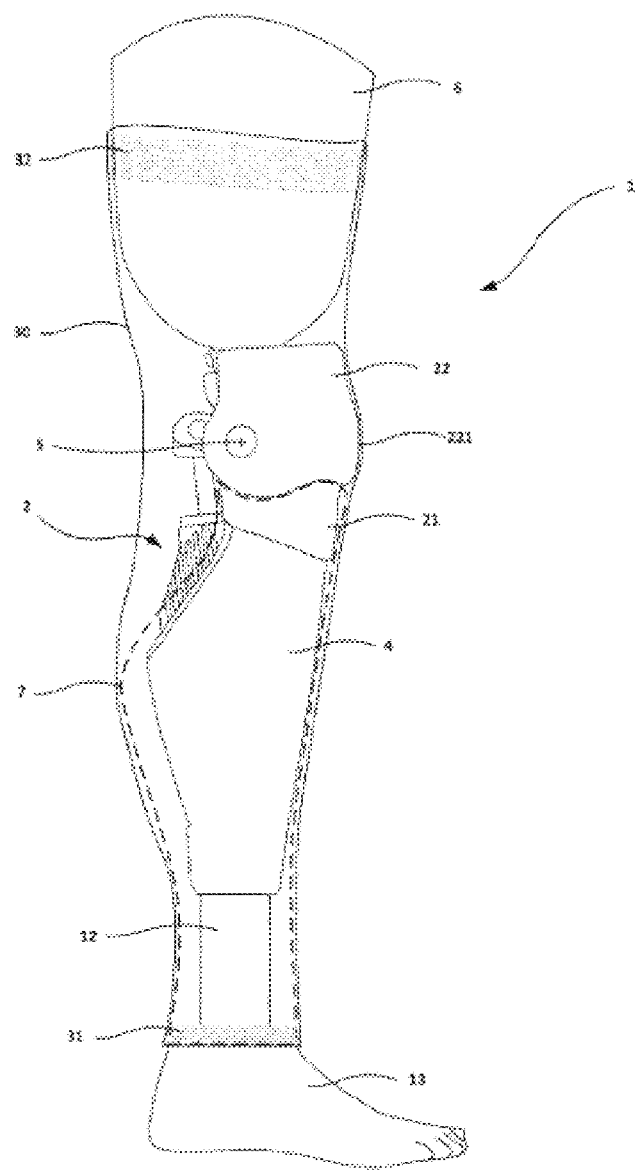

US 11,051,956 B2

PROSTHESIS COSMETIC ELEMENT, AND SYSTEM CONSISTING OF PROSTHESIS COSMETIC ELEMENT AND PROSTHESIS

TECHNICAL FIELD

The invention relates to a prosthesis cosmetic element for a prosthesis having a prosthesis joint which has an upper part and a lower part mounted thereon in a pivotal manner about a pivot axis, as well as a system comprising a prosthesis cosmetic element and a prosthesis. The prosthesis cosmetic element is particularly suitable for covering prostheses of the lower limb, particularly for covering prosthetic legs in patients with a thigh stump. Such prosthesis cosmetic elements can, in principle, also be disposed on an upper extremity, particularly in patients with an upper arm stump and a prosthetic elbow joint.

BACKGROUND

Prostheses serve as a replacement part for non-existing or no longer existing natural limbs and have the purpose of reestablishing or at least in part reestablishing lacking or lost functionality. In addition, purely decorative prostheses are also available and intended to conceal a missing natural limb. Prostheses with a prosthesis joint include means for fixing the prosthesis joint to the stump; said means fasten the upper part of the prosthesis joint to the stump by means of a prosthesis socket. Several options are available for achieving this. A lower part is pivotably disposed on the upper part, and further prosthetic components can be fastened to the lower part. For example, dampening devices, actuators and other prosthetic components, such as lower-leg tubes, prosthesis hands or prosthesis feet may be attached. These prosthetic component designs are primarily concerned with functional aspects; the used materials should be durable, adequate for handling the required load, and lightweight. As a result, the appearance of a prosthesis is typically consistent with technical concerns.

To approximate the appearance of a prosthesis to the appearance of the missing limb, so-called prosthesis cosmetic elements are disposed on the prosthesis that characterize the appearance of the prosthesis. The prosthesis cosmetic element can be made of different materials and can also include technical functionalities; for example, protection against mechanical effects and environmental impact as well as, to a limited extent, reset forces, if the cosmetic appearance was changed due to deformation during a moving action of the prosthesis. Foam is often used as a material for fashioning prosthesis cosmetic elements, which have to be modulated to match the external contour of the limb they are to replace. An elastomer coating can be applied over the foam intended to simulate a skin-like appearance. Accordingly, the foam materials are coated with so-called cosmetic skins that, after heating, must be applied and shrunk onto the foam base or glued thereon.

WO 2010/054341 A1 teaches a method for manufacturing customized devices or prosthetic covers that requires reference points to be marked on the body. A plurality of images is taken from a plurality of angles and used to record the contour of the body contours. The other markings are applied and used for manufacturing the cosmetic element. The cosmetic element can be constructed in one piece or in multiple pieces that must be installed.

U.S. Pat. No. 5,880,964 A relates to a system and method for producing a prosthesis cosmetic element that provides that the prosthesis is attached to the user. The data for the socket and components of the prosthesis are stored in a database. These data are used for calculating the dimensions of the internal surface of the prosthesis cosmetic element. Using CAD systems, an external contour is produced by means of an automated grinding method matching the contour of the limb on the untreated side of the body.

SUMMARY

U.S. Pat. No. 6,597,965 A relates to a method for producing a cosmetic foam element for a prosthetic component. Two halves of an internal cavity are calculated based on the data of the prosthetic component. A computer-controlled grinding machine cuts a part of the one half of the cavity in one side of the block and a part of the other half in the opposite side of the block. The block is cut in half and the two halves that are opposite each other are joined in such a way that the block encloses the prosthetic component and accommodates the prosthetic component inside the assembled cavity.

U.S. Pat. No. 6,740,124 A relates to an endoprosthesis for transfemoral amputees; it includes a socket, a foam-covered pylon and a prosthetic foot. A plastic shell is molded, heated and stretched until it has a shape that can envelop the foam. Areas with poor fit are spot-heated with hot air.

U.S. Pat. No. 8,366,789 B1 relates to a prosthetic means with an external surface that mirrors the surface of the healthy leg. The healthy limb is scanned, and the obtained data are processed to establish a corresponding contour. The design data of the prosthetic means are processed in the context of rapid prototyping, and a cosmetic element is produced. The prosthesis cosmetic element extends over the area of the socket and the prosthesis joint.

DE 20309318 U1 relates to a knee portion partition adapter for detachably connecting a first cosmetic foam part that can be pushed over a knee joint of a prosthetic leg and pulled over a femoral socket. A second cosmetic foam part is disposed around a lower leg part of the leg prosthesis. Two detachably connectible, plate-like adapter parts are provided, wherein a first adapter part with the first cosmetic foam part and a second adapter part with the second cosmetic foam part are detachably connected. The foam part completely encloses the prosthesis joint.

U.S. Pat. No. 5,376,127 A relates to a light-weight prosthesis cosmetic element with a contour and appearance of a human limb. The cosmetic element is disposed around a prosthetic component and is produced by heating and shaping a prefabricated closed-cell polyethylene sheet material.

US 2007/0150069 A1 relates to a modularized leg prosthesis cosmetic element with a thigh module that can be fixed in place on a thigh socket, a lower leg module that can be fixed in place to a lower-leg tube, and a patellar module that is pivotably connected to the lower-leg module. The cosmetic element, which is achieved by fastening the modules to each other, is covered by a skin module made of a stretchable fiber.

US 2007/0162154 A1 relates to an orthopedic prosthesis cover for a prosthesis part with a hollow, substantially cylindrical base body that accommodates the prosthetic component therein, and with an opening of adequate size to allow for a prosthetic knee to bend. The width is appropriately dimensioned to provide protection for the mechanical components of the prosthesis knee joint.

DE 10 2012 009 757 A1 relates to a prosthetic means and a cover for a prosthetic means that allows for customizing the external contour of the prosthetic means. A rotary module is used for rotating a lower part relative to an upper part of a first part of a prosthetic means about a longitudinal axis thereof. The goal is to achieve an aesthetic cover in the rotated state.

Prosthesis cosmetic elements that are known from the prior art often suffer from the problem that they do not extend beyond the joint area, wherefore they do not cover relative movements that occur between the upper part and the lower part. Mere foam casings are susceptible to accumulating dirt and pose a resistance, due to the material's strength and elastic properties, relative to flexing and extension actions. Moreover, it is difficult to pull foam covers quickly on and off to replace a used cover, as needed.

It is the object of the present invention to provide a prosthesis cosmetic element, and a system consisting of a prosthesis cosmetic element and a prosthesis that allows for the possibility of providing a cover across the joint area but without having to accept significant limitations in terms of the operability of the prosthesis.

According to the invention this object is achieved by a prosthesis cosmetic element having the features of the main claim and a system with the features of the coordinate claim. Advantageous improvements and variants of the invention are disclosed in the dependent claims, the description and the figures.

The prosthesis cosmetic element according to the invention for a prosthesis having a prosthesis joint, which has an upper part and a lower part that is mounted thereon in a pivotal manner about a pivot axis, provides that the prosthesis cosmetic element includes a first frame part having at least one securing means for fastening it to the lower part. Moreover, the prosthesis cosmetic element includes a second frame part having at least one securing means for fastening it to the upper part, wherein the two frame parts are pivotably supported relative to each other. A rotational element or rotary adapter is disposed on the prosthetic joint and preferably on a frame part, wherein the adapter is configured to have the capacity of being locked or unlocked by an actuating element. The actuating element is accessible from the outside by a frame part or through a frame part. The actuating element opens or closes a blocking or locking means within the rotary adapter, whereby it can, when the prosthesis is in the attached state, and provided with a textile cover, implement a change in the alignment of the prosthesis cosmetic element from the outside by means of rotating and/or pivoting one part of the frame relative to another, particularly relative to a head area. If settings are to be applied inside the prosthesis cosmetic element, it is advantageously envisioned that at least one recess or at least one actuating element is disposed thereon through which a setting can be applied from the outside.

The rotational element can be enclosed at least partially by at least one frame part, wherein the rotational element can be actuated through the at least one frame part or by the at least one frame part. To this end, the rotational element is preferably fastened to one of the two frame parts. In particular, the rotational element can be fastened to the upper part and/or the second frame part to facilitate accessibility and a reliable assignment.

One improvement according to the invention provides that at least one of the two frame parts include a head area that is configured at least partially as ball-like or barrel-like and that is rotatably supported in the other frame part. The prosthesis cosmetic element is envisioned particularly for prosthesis elbow joints or prosthesis knee joints and includes a frame with ball-like or partially ball-like and/or barrel-like or partially barrel-like head areas in the joint area, so that, even in a flexed state, a contour that approximates the natural appearance is provided. The frame parts form a substructure for disposing further components of the prosthesis cosmetic element. The respective frame part is fastened to the upper part or lower part of the prosthesis knee joint or mounted to further components of the prosthesis joint, whereby the movement of the upper part or lower part is also executed with the respective frame part. The head area of the first frame part on the lower part is proximally configured; a head area of the second frame part is distally configured. Preferably, the head area of the first frame proximally protrudes the pivot axis. The frame part accommodates functionally crucial components of the lower part or of prosthetic components downstream of the lower part that are disposed thereon; for example, a lower-leg tube, a dampening device or an actuator. The frame leaves space for accommodating upper and lower connection means; for example, a pyramid adapter or screwed connection for a lower-leg tube, lower-arm tube or prosthesis socket. Such a connection modality allows for cosmetic bridging of the joint connection and the socket.

An improvement according to the invention envisions that a partially ball-like or partially barrel-like head area be configured on both frame parts, meaning on the first frame part and the second frame part, which cover the joint at least partially when the joint is in an extended position, and wherein one head area receives the other head area therein. As a result, in the extended position, there exists at least partially double coverage of the prosthesis joint means, which is why it is possible to achieve particularly good protection of the prosthetic means in conjunction with a natural appearance.

In a further improvement according to the invention, when the prosthesis joint is in a flexed position, it is envisioned that the head areas are supplementing one another, and they are at least partially surrounding the prosthetic joint. In one prosthesis knee joint, the head areas are preferably disposed and dimensioned in such a manner that the head areas are overlapping or flush relative to each other even in a maximally flexed position. The goal is to prevent any gap from forming that would give access from between the two frame parts to the joint means that is disposed there-behind. The cover is closed to the front, thereby flexing action continues to be possible.

This embodiment prevents any cosmetic cover, which has been applied onto the frame parts, from becoming pinched during the movement of the prosthesis joint. The same applies with regard to an application involving a prosthetic elbow joint.

The first frame part can be configured as shell-like or with struts that extend in longitudinal extension of the lower part. For a shell-like configuration of the first frame part, a fully two-dimensional cover is configured in the area of the shell-like cover that is parallel or longitudinal relative to the lower part and a prosthetic means downstream, such as a lower-leg tube or a prosthesis joint having a mechanical, hydraulic or actuator means, to provide, on the one hand, a smooth contour and, on the other hand, a high level of mechanical protection. Using a shell-like or groove-like configuration, whereby the front side of a lower-leg tube is covered, for example, it is possible, on the one hand, to simulate a contour of the natural extremity and, on the other hand, provide mechanical protection.

As an alternative to a shell-like and therefore two-dimensional cover, one variant envisions that at least two struts or strips extend away from the head area; specifically, they extend in longitudinal extension of the lower part and/or the prosthetic component downstream of the lower part and thereby enable a fixation to the lower part or the prosthetic component. The struts or strips are advantageously formed in one piece with the head part; and they preferably extend medially and laterally relative to the lower part. This configuration ensures that the first frame part is not located at locations that are subjected to extreme stresses in the knee area, so that the frame part does not have to absorb any major forces, for example, when kneeling or bracing. Thus, the frame part can be designed as being very light.

The first frame part proximally extends beyond the pivot axis to generate the natural appearance in the flexed state. Moreover, the protrusion provides a mechanical protective means for the prosthetic components located there-behind.

The second frame part can include at least one bridging element or at least one bridging section, wherein the bridging element or bridging section extends in the direction of a prosthesis socket, by which the prosthesis is fixed in place on the stump. Often there is a free space between the prosthesis socket and the upper part that is bridged by a connecting piece; for example, a tube, a rotational element or rotary adapter, or the like. The connecting piece is fixed in place by the proximal end thereof via a tubular adapter to the prosthesis socket, and by its distal end, via a corresponding adapter, it is fixed in place to the upper part of the prosthesis joint. The diameter of the connecting piece is smaller than the diameter of the prosthesis socket; this means, if a cosmetic cover is applied, when a flexing motion is performed, the contour changes such that an indentation forms on the upper side. To prevent this, a bridging section is formed on the frame that can extend, for example, all the way to the prosthesis socket.

The bridging section can be configured on the second frame part. A bridging element is preferably fastened to the second frame part and extends to the prosthesis socket, or to the immediate vicinity thereof. It is also possible for the bridging element and/or bridging section to be fastened to the prosthesis socket. Accordingly, the end of the bridging element or of the bridging section that faces away from the frame part includes a corresponding means, for example, a positive locking element or a force fitting device, such as, for example, magnets, adhesive sections, or the like. Possible positive locking elements that can be disposed on the prosthesis socket and the bridging element or bridging section are snaps, hooks, clips, screws or rivets.

The bridging section and/or bridging element can be rotatably mounted on the second frame part or on the prosthesis socket. Rotatable mounting facilitates any belated aligning of the prosthesis cosmetic element and/or frame parts relative to the prosthesis socket or relative to a cover. Rotatable mounting can be implemented by means of a rotary adapter that enables rotation about the longitudinal axis of the upper part as well as tilting, for example, about a horizontal axis. This allows for the following modifications in the structural setup of the prosthesis knee joint. By enabling a rotational motion and tilting motion, it is possible to enable undisturbed rotational motion and alignment between the prosthesis socket and the joint without there being a malfunction relative to the settings of the prosthetic structural setup. Due to the rotational motion and advantageously also due to the tilting motion, any changes are neutralized that may occur in the structural setup of the prosthesis due to a shift in the coaxiality of the vertical joint axis and the axis of rotation of the rotary adapter.

A receiving means for a contour-forming molded part can be disposed on the first frame part; particularly, a foam part or a molded part made of a two-dimensional material can be fastened to the lower first frame part for customizing the contour of the prosthesis cosmetic element by means of a frame part design.

According to an improvement of the invention, the head area is configured as a separate component that can be fastened separately to the frame part. In this way, it is possible to provide different shapes or sizes, whereby a modular structural setup of the frame parts can be achieved. It also improves the approximation relative to the natural appearance.

A textile cover is advantageously pulled over the frame parts, thereby covering up the frame parts. The textile cover offers the advantage that only minimal mechanical forces, or none at all, are transferred to the prosthesis joint. Complex shrinking or gluing processes in order to apply skin-like sheeting to a foam body are no longer necessary, since the frame-type construction provides a form-giving substructure, which must now only be provided with a quasi-closed surface, similarly to a stocking. The textile designs are varied; a skin-colored cover like a pantyhose can be envisioned, just like different-colored materials. The textile cover can be fastened by positive locking or force fitting elements, such as elastic bands, adhesive elements or adhesive areas on the frame and/or the further prosthetic components. The fixation can take place just on the frame or also on the prosthetic component, such as on the prosthesis socket or a distal prosthetic element, such as a prosthesis hand or a prosthesis foot. Corresponding means are provided on the respective prosthetic components to ensure that the textile cover can be fastened thereto. In one embodiment of the positive locking elements as hook-and-loop fasteners, corresponding fleece or hook areas are provided in the respective fastening areas.

The textile cover can also have partial areas where the material is thickened, stiffeners or reinforcements can be applied to or incorporated in the cover, so as to provide a contour-forming feature, as well as a functional component in addition to a purely surface configuration.

Instead of a textile cover, the use of other cover materials is also possible.

Alternatively, or in addition, it is possible to fasten or apply, on the inside of the frame parts, a coating that is made of an elastic material, for example, rubber, to dampen or prevent vibrations that can be generated when a rigid frame material is used and that can be transferred to the knee joint. It helps to reduce, or prevent altogether, any noise generation, so-called humming. The coating can protect the frame and the lacquering thereon.

By fixation and spacer elements the frame part can be fastened to the prosthesis or kept spaced relative to the prosthesis. Fastening elements are, for example, a strap or a flexible traction means; spacer elements are, for example, a metal stirrup with a plastic part, disks, pins, or projections, if need be, made as elastic components, to achieve adequate volume stability or positional stability of the frame part relative to the prosthetics component that is disposed therebelow, for example, a tube or a socket. For the embodiment as metal stirrup, the spacer element is preferably fastened to the upper part and secured against any rotation.

The frame parts are preferably made of dimensionally stable materials, particularly metal, fiber-reinforced plastics, thermosetting plastics or thermoplastics or of a foam material, which means, aside from a pure contouring function, mechanical stresses can be absorbed as well.

The invention also relates to a system consisting of a prosthesis cosmetic element, as described above, and a prosthesis having a prosthesis joint which has an upper part and a lower part mounted thereon in a pivotal manner about a pivot axis, wherein a rotational element is disposed on the prosthesis joint that has disposed thereon an actuating element which is accessible from the outside.

BRIEF DESCRIPTION OF THE DRAWINGS

Embodiments of the invention will be explained in further detail in reference to the accompanying figures. Identical I reference numerals refer to the same or similar components. Shown are as follows:

FIGS. 1a-1c show a schematic representation of a prothesis cosmetic element seen in different views;

FIG. 2 is a schematic representation of a prosthesis with a prosthesis cosmetic element seen in a side view;

Figure 1A:
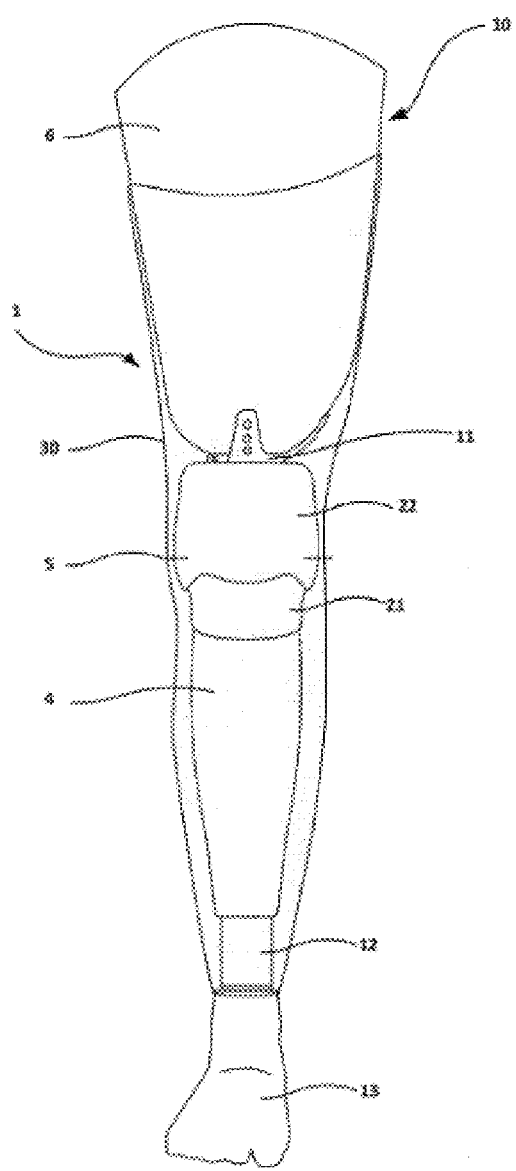

DETAILED DESCRIPTION 1a shows a schematic frontal view of a prosthesis cosmetic element 1 for a prosthesis 10; in the illustrated embodiment, for a prosthetic leg with a prosthesis socket 6 that is to be fitted on a thigh stump, which is not seen here. The prosthesis 10 includes a prosthesis joint 2 in the form of a prosthesis knee joint that includes an upper part 3 and a lower part 4 pivotably attached thereto about a pivot axis 5. On the lower part 4, a prosthesis foot 13 is attached to a lower-leg tube 12 as distal termination of the prosthesis 10. Instead of in a prosthesis knee joint 2 and a prosthesis foot 13, the prosthesis cosmetic element 1 can also be disposed and configured in an arm prosthesis; in this case, instead of a thigh socket, an upper arm socket and instead of a prosthesis knee joint, an elbow joint and instead of a prosthesis foot, a prosthesis hand are provided. The remarks below shall apply correspondingly also for a prosthesis of the upper extremity.

The upper part 3 of the prosthesis knee joint 2 is connected via a connecting piece 11, such as, for example, a rotary adapter or a tube, to the thigh socket 6. A cover 30 is disposed on the exterior of the thigh socket 6; in the depicted embodiment, this is a textile cover 30 that extends across the joint region and about the pivot axis 5 to the proximal end of the prosthesis foot 13. The cover 30 can be fastened to the respective prosthetic component by means of a positive lock or a force fitting; in the depicted embodiment it is fastened to the prosthesis socket 6 and the prosthesis foot 13, for example, by means of magnets, hook and loop fasteners, clips, screws, rivets, adhesive element or sticky means.

The prosthesis cosmetic element 1 provides a first frame part 21 that is fastened to the lower part 4. The first frame part 21 extends proximally beyond the pivot axis 5. A second frame part 22 is disposed on the upper part 3; in the depicted embodiment, this frame part extends distally beyond the pivot axis 5 and overlaps in the depicted embodiment the proximal edge of the first frame part 21. A bridging section 223 is configured on the second frame part 22 extending in the proximal direction; and said bridging portion 223 extends in the direction of the prosthesis socket 6 to provide an approximately even and an, as much as possible, seamless contour from the thigh socket 6 to the prosthesis knee joint 2. The bridging section 223 is depicted in FIG. 1b, which shows a side view of the prosthesis 10 without cover 30. In addition to a single bridging section 223, it is possible to dispose or configure a plurality of bridging sections 223 on the second frame part 22, for example, as tabs, tongues or projections. The one or more bridging sections 223 mask the difference in the diameters of the external diameter of the prosthesis socket 6 and the connecting piece 11 for connecting the prosthesis socket 6 to the prosthesis knee joint 2.

Aside from means for connecting proximal or distal prosthetic components, such as the prosthesis socket 6 and lower-leg tube 12, the prosthesis knee joint 2 can also include damping elements, actuators and mechanical or electrical and electronic control components. In the embodiment according to FIG. 1b, the lower part 4 is covered by a molded part 7 that is modeled into the shape of a natural leg. The molded part 7 can be made of a foam material; it can be covered with a cover 30, as shown in a frontal view in FIG. 1c. The first frame part 21 can be configured as open toward the front, whereby a window is formed in the area of the natural tibial head to prevent a mechanical load from being applied to the first frame part 21, for example while kneeling down, when a frontal load acts on the prosthesis knee joint 2.

FIG. 2 shows a side view of a variant of the invention where the prosthesis cosmetic element 1 is depicted on a prosthetic leg in an extended position. The cover 30 is fastened to the outside of the prosthesis socket 6 by means of a force fitting locking element 32, which is an elastic band with a sticky inner side. In the alternative, instead of a band 32, an area with a sticky coating made of, for example, silicone, can be attached on the inside of the cover 30. The prosthesis socket 6 is coupled to the prosthesis knee joint 2 by means of a connecting element that is embodied as a rotary adapter, shown in part. The second frame part 22 is fastened to the upper part of the prosthesis joint 2, whereby, when the prosthesis socket 6 moves, the second frame part 22 is taken along. A head area 221 is configured at the distal end of the second frame part 22, said head area is shaped like a partial ball or like a partial barrel, and this corresponds substantially to the natural shape of a knee joint. The first frame part 21 is fastened to the lower part 4 of the prosthesis knee joint 2 so that when a swinging action about the pivot axis 5 occurs, the first frame part 21 together with lower part 3 and any prosthetic components downstream thereto, such as the prosthesis foot 13 or a lower-leg tube 12, are moved as well. A molded part 7 or a plurality of molded parts 7 are posteriorly fastened to the first frame part 21 for simulating a natural calf musculature. The distal end of the cover 30 is fastened to the prosthesis foot 13 by means of a positive locking element 31, which is a hook and loop fastener in the present context. As a matter of principle, the use of other connecting elements is also possible for fastening the cover 30 on the prosthesis foot 13, the lower-leg tube or the frame part 21, for example by means of the above-described force fitting elements or by a region with an applied sticky coating on the inside of the cover 30. The textile cover 30 extends from the thigh socket 6 to the proximal end of the prosthesis foot 13.

Figure 3:
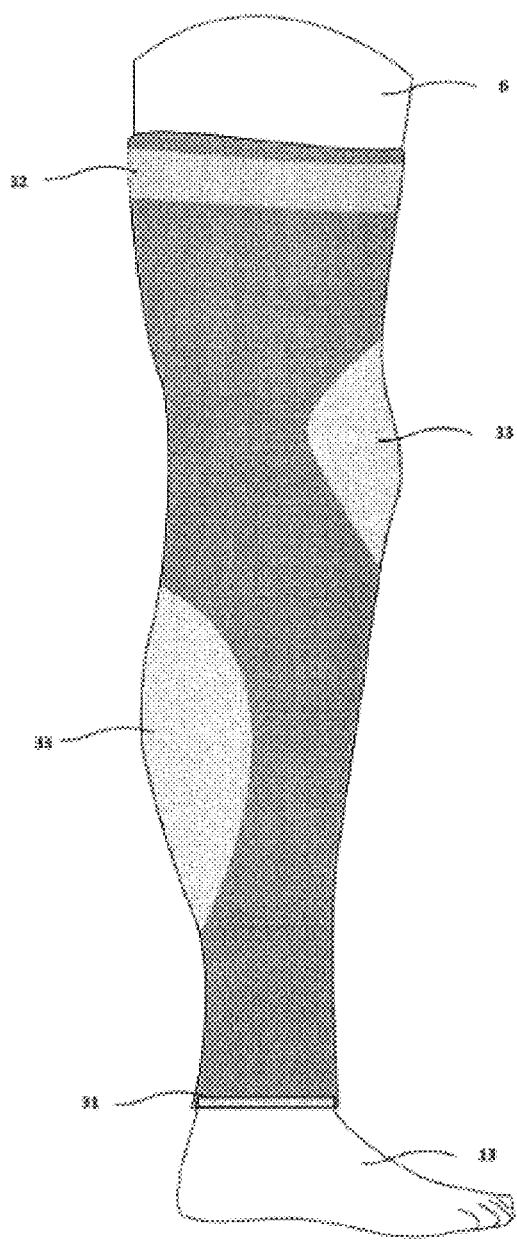
FIG. 3 is a variant of FIG. 2 with a textile cover.

In FIG. 3, a side view of the prosthesis 10 is depicted with a prosthesis cosmetic element together with the textile cover 30. The textile cover 30 is used in combination with the two frame parts 21, 22 enabling easy donning and doffing of the cover. Due to the textile embodiment, the cover 30 can be easily applied to the prosthetic components 6, 13 and/or the frame parts 21, 22. If a molded part 7 is disposed on the lower part 4, preferably, the textile cover 30 can be attached to said molded part 7 by means of an adhesive silicone connection, which means at least by a partial silicone coating on the cover 30 and/or the molded part 7. The user of the prosthesis cosmetic element 1 thus has the option of choosing and wearing different designs for different types of occasions. The suggested basic color is a design that approximates the color of skin. The cover 30 can easily be pulled over the entire prosthesis 10; similarly, the cover 30 can be designed as open along the longitudinal extension thereof and be equipped with closure elements, such as, for example, a zipper or hook-and-loop closure. An inside coating featuring an elastomer or a silicone prevents slippage on the surface of the prosthesis and the frame construction. Using an adapter part, it is also possible to connect the textile cover 30 directly in a foot casing, thereby allowing the textile cover to be utilized without the foot part but also coupled to a sock-like cover for the prosthesis foot 13, as needed. Stiffeners 33, partial areas featuring thickened materials or reinforcements, are arranged on the cover 30 in the shown embodiment, in the area of the knee and the calf. Stiffeners or reinforcements can also be arranged within the cover 30.

Figure 4:
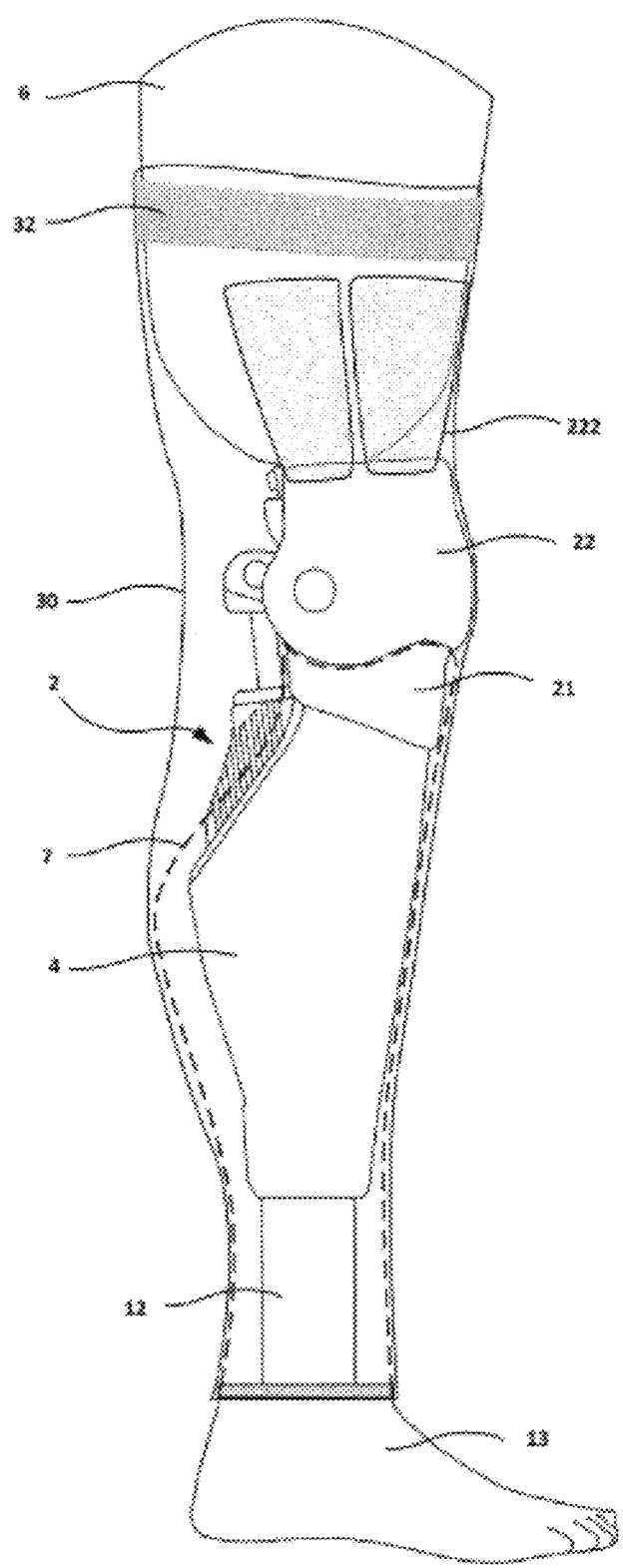
FIG. 4 is a prosthesis according to FIG. 3 without textile cover.

FIG. 4 shows a side view of the embodiment of the prosthesis 10 and prosthesis cosmetic elements with the cover 30. The prosthesis socket 6 is connected to the prosthesis knee joint 2 by means of the connecting element 11. The second frame part 22 is fastened to the upper part 3 by means of a fastening element that is not shown here. Bridging elements 222, in the form of belts, plates or tabs, extend from the second frame part 22 to the prosthesis socket 6. The bridging elements 222 are fixed in position on the prosthesis socket 6 by positive locking, material locking or force fitting means. The first frame part 21 is disposed underneath the second frame part 22 and is connected to the lower part 4. Fastening is achieved, on the one hand, in the area of the pivot axis 5 and, on the other hand, in the distal area on the lower-leg tube 12, for example, by means of clips or snap connections. The attachment to the lower-leg tube 12 can also be achieved in different ways. A molded part 7 is detectable in the distal area of the first frame part 21 with the simulated shape of a natural calf; in the depicted embodiment, it is modeled from a flat material having a corresponding shape. Alternatively, the molded part 7 can also be modeled from a foam element that is fastened to the frame part 21 by means of fastener elements, such as clips, hook and loop fasteners, adhesive connections, screws, rivets, commonly by means of a positive lock or also a magnetic fastening.

Figure 5:
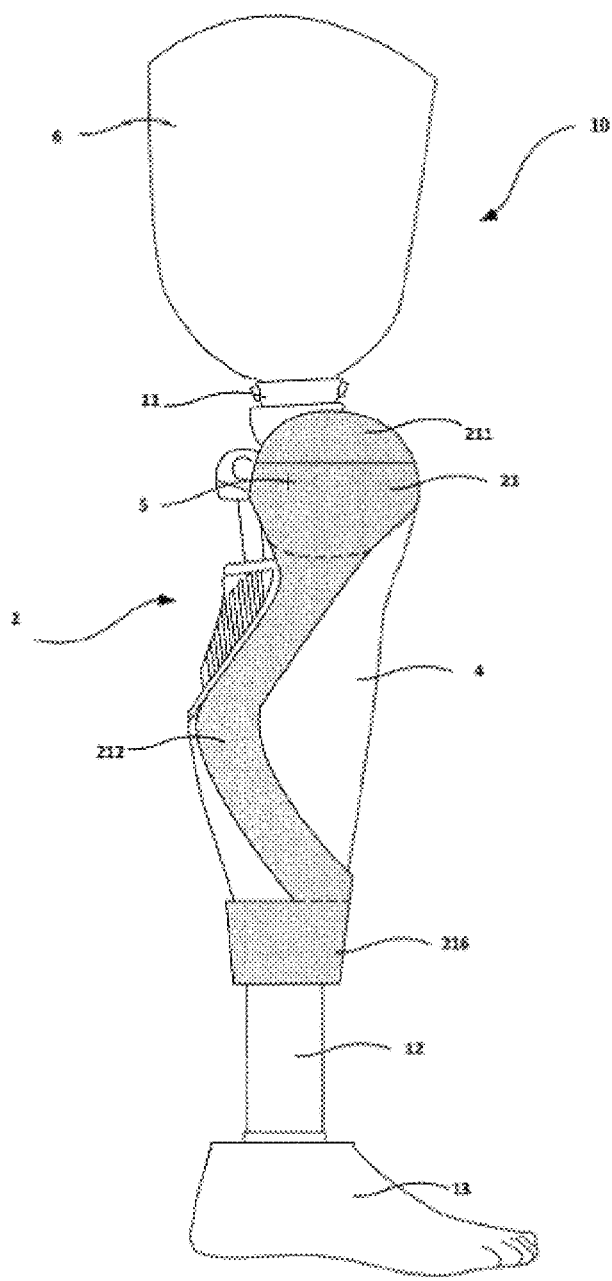
FIG. 5 is a schematic view of a first frame part.

FIG. 5 shows a variant of the first frame part 21 in the mounted state with the lower part 4 of the prosthesis knee joint. The first frame part 21 is configured in one piece and includes a semi-ball-like head area 211 that extends proximally over the pivot axis 5 of the prosthesis knee joint. The first frame part 21 is configured as a lightweight component resting closely against the lower part 4, which is why the overall profile is a narrow silhouette. FIG. 5 depicts the first frame part 21 in a side view, and the front and rear parts of the lower part 4 are not covered by the first frame part 21. Two struts 212 extend medially and laterally from the partially ball-like head area 211, all the way to a distal clip or clamp 216 that provides further fastening action to the lower part 4. The proximal head area 211 includes a recess for the connecting element 11 in the form of a rotary adapter, whereby it is possible to easily push the first frame part 21 onto the lower part 4 fastening the same thereto by means of a snapping or clamping mechanism. In the bent state, the partially ball-like head area 211 substantially simulates the natural shape of a knee. According to FIG. 5, the frontal area of the lower part 4 is free so that no forces are introduced into the first frame part 21 while kneeling down.

Figure 6:
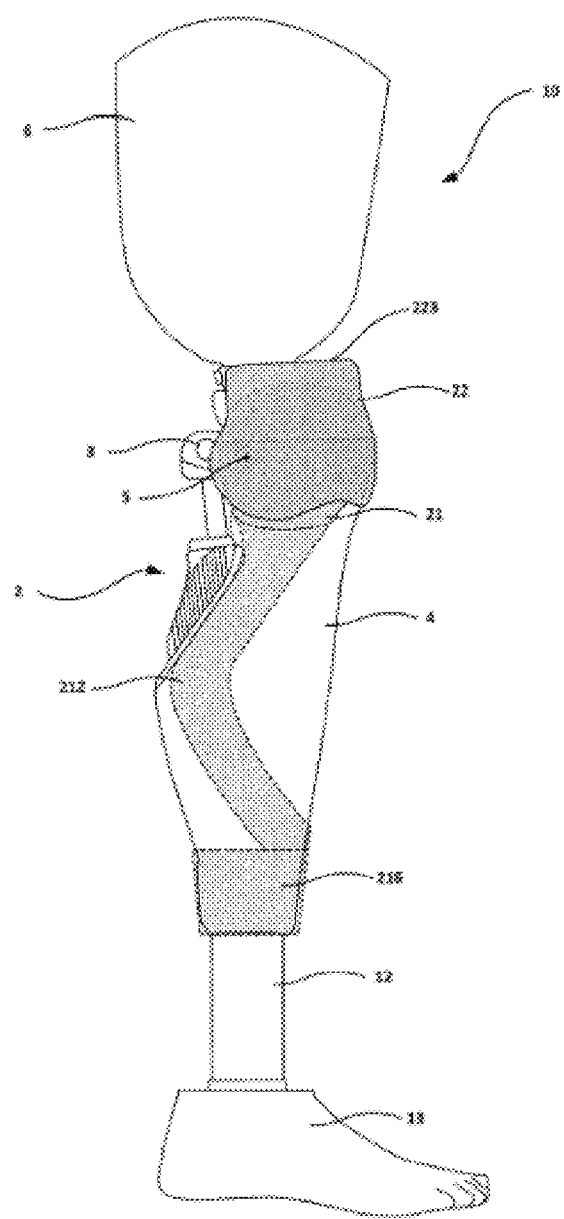
FIG. 6 is a schematic view of a prosthesis according to FIG. 5, with a second frame part.

FIG. 6 shows the second frame part 22 in connection with the first frame part according to FIG. 5, wherein the second frame part 22 is fastened to the upper part 3, and whereby, during a flexing motion, it is swung about the pivot axis 5 together with the prosthesis socket 6. The first frame part 21 is indicated by dashed lines. In the extended state, the second frame part 22 overlaps the head area 211 of the first frame part, whereby, when a pivoting motion occurs, the partially ball-like head portion 211 rotates within the second frame part 22. The gap or tolerances between the first frame part 21 and the second frame part 22 are as minimal as possible, wherefore any pinching of a cover 30 in a space between the first frame part 21 and the second frame part 22 can be precluded. Bridging sections 223 or a bridging section 223 are configured on the second frame part 22 and extend in the direction of the prosthesis socket 6 equalizing the volume between a cover 30 and the connecting piece 11, for example a rotary adapter or thigh tube, whereby a cover 30 maintains the contour of a natural extremity. The second frame part 22 is preferably closed on the front. Similarly, the head area 211 of the first frame part 21 is also closed on the front; only a slot is provided for pivoting the upper part 3 about the pivot axis 5, which is why a contour that is almost completely closed is achieved in the frontal area of the prosthesis cosmetic element 1, both during standing as well as in the flexed state.

Figure 7:
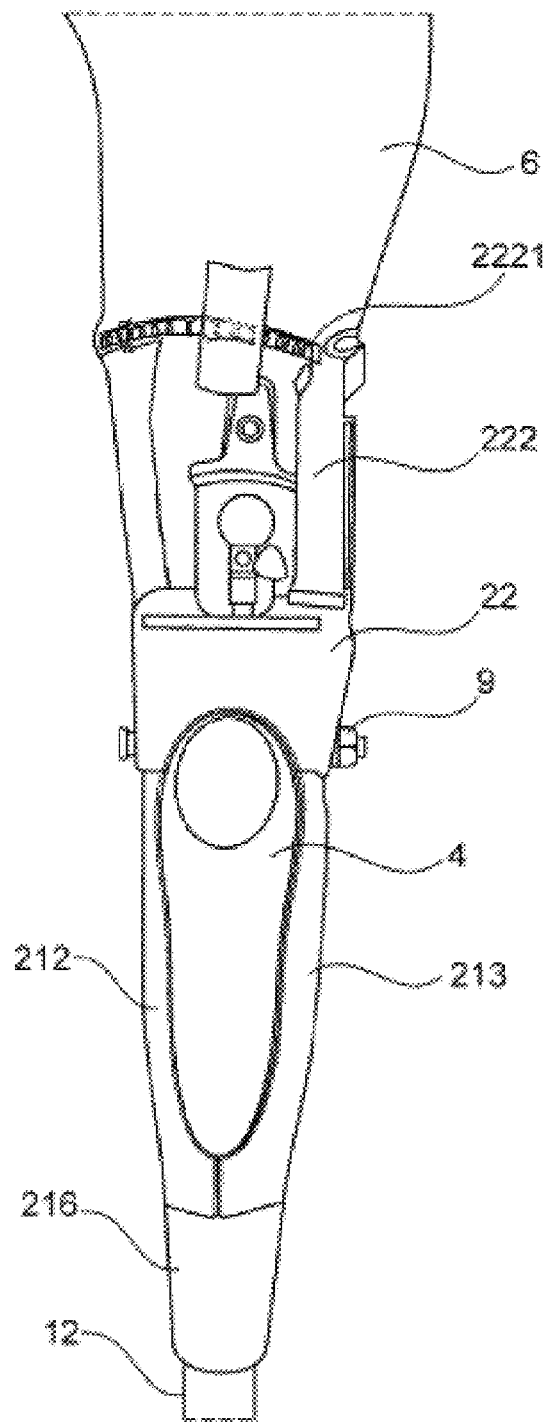
FIG. 7 is a front view of a prosthesis cosmetic element without textile cover in an extended position.

FIG. 7 shows a frontal view of the prosthesis cosmetic element 1 without textile cover. The first frame part 21 is fastened to the lower part 4 by means of fastener elements 9 in the form of axes for inserting, bolts or nuts. In the distal section, fastening action is achieved by means of a click-type closure, a snap-type closure or other fastener means. Proximally of the pivot axis 5, the second frame part 22 is disposed with a frontally closed shaping. Likewise, the second frame part 22 is pivotally fastened about the pivot axis 5 by means of fastening element 9 in the form of axes for inserting the prosthesis. Using the bridging elements 222 in the form of strips of fabric that are fastened by means of force fitting elements 2221, in the form of a silicone, spring band or a rubber band to the prosthesis socket 6, a force transfer to the second frame part 22 is achieved, whereby, during flexing, the second frame part 22 as well as the bridging elements 222 are moved therewith. Instead of strips made of fabric, the bridging elements 222 can also use plastic, foam or metal materials that can be configured in a strip or similar form. An adapter connection for connecting the connecting piece 11 to the prosthesis socket 6 is shown within the bridging elements 222.

Figure 8:
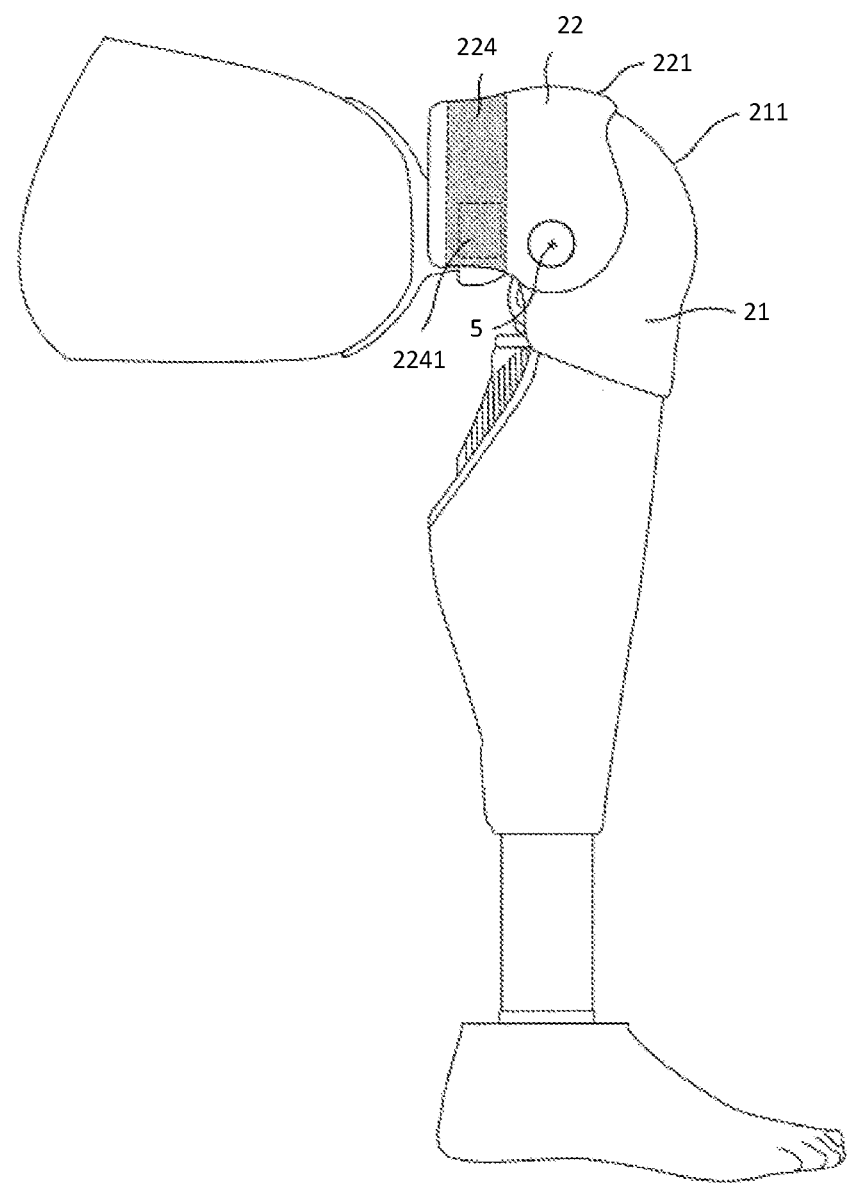
FIG. 8 is a prosthesis in a bent position seen in a side view.

FIG. 8 shows a variant according to the invention having a first frame part 21 that is configured as a fully two-dimensional, shell-like frame part 21. The partially ball-like head area 211 follows proximally relative to the shell-like tibial part, over which the distal head area 221 by way of a partially ball-like design of the second frame part 22 is disposed, whereby, when a pivoting movement is performed by the lower part relative to the upper part, the partial calottes of the head areas 211, 221 glide over each other, and form a complementary partial ball in the flexed state. A rotary adapter 224 is disposed on or in the proximal end region of the second frame part 22; bridging elements 222 or also the bridging areas 223 can be disposed or configured on the rotary adapter. The rotary adapter 224 can enable a relative motion about at least one pivot axis, particularly about the longitudinal axis of the upper part 2, to enable, if the prosthesis socket 6 is tilting or turning relative to the prosthesis knee joint 2, optimal positioning of the upper frame part 22. As a matter of principle, it is also possible to provide a rotary adapter within the prosthetic means to enable rotation and tilting of the prosthesis socket relative to the upper part. To ensure accessibility, accordingly, it is possible to provide cutouts 2244, holes or open positions and actuating elements 2241 in the second frame part 22 by which the rotary adapter 224 or the rotary adapter that is disposed in the prosthesis device is accessible and operable. In this way, it is possible to render the respective rotary adapter 224 accessible from the outside. The actuating element 2241 is used to activate and deactivate and/or to lock and unlock the rotary adapter 224 on a prosthesis joint with installed frame parts 21, 22.

In the embodiment according to FIG. 8, the characteristics of the self-supporting structure of the frame are visibly revealed. The advantageous aspect therein is the freedom from the used knee joint and the weight reduction of the prosthesis knee joint.

Figure 9:
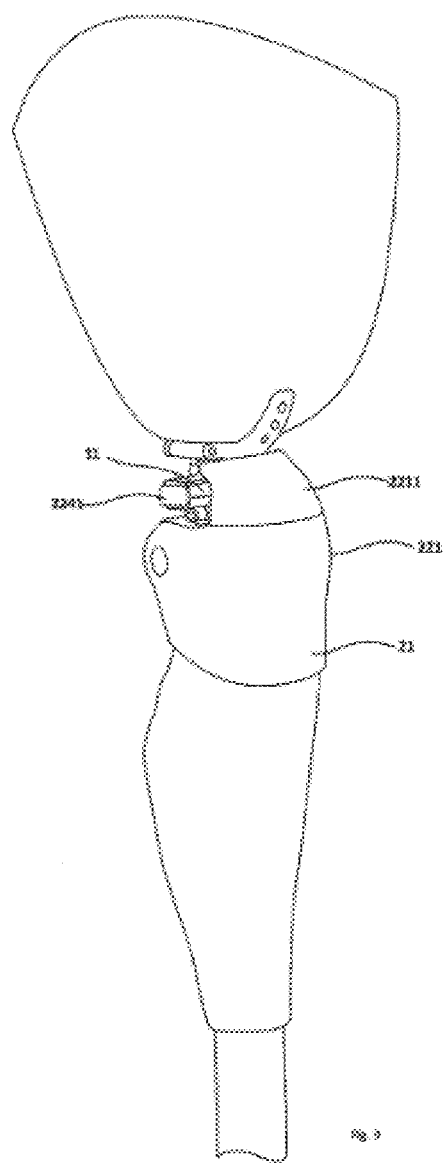
FIG. 9 shows mounted frame parts in an extended position, with rotary adapter in a side view.

FIG. 9 shows a further variant of the first frame part 21 having disposed thereon a head portion 211 with an extension 2211 formed thereon or disposed as a separate component 2211 and to which the frame part 21 is fastened. The fastening action can be achieved by pushing on or clicking on means or by screws, rivets or other fastener elements. Advantageously, the extension 2211 can be reversibly mounted to the head area 221 on the first frame part 21. A significant advantage of such a modular solution is that it is also suitable for accommodating long thigh stumps or knee disarticulation prostheses. The head area 211 and the extension 2211 are substantially configured as ball-like or barrel-like; here too, the ball-like or barrel-like shape serves primarily the purpose of the shaping design and as protection against pinching of the cover. The extension 2211 that is disposed at the proximal edge of the head area 211 continues the partially ball-like contour of the front edge of the first frame part 21 to top rear. The head area 211 and the extension 2211 cover, at least in the extended position, the connecting element 11 in the front; preferably also when the prosthesis joint is flexed, so that an at least approximate natural knee contour is achieved.

Figure 10:
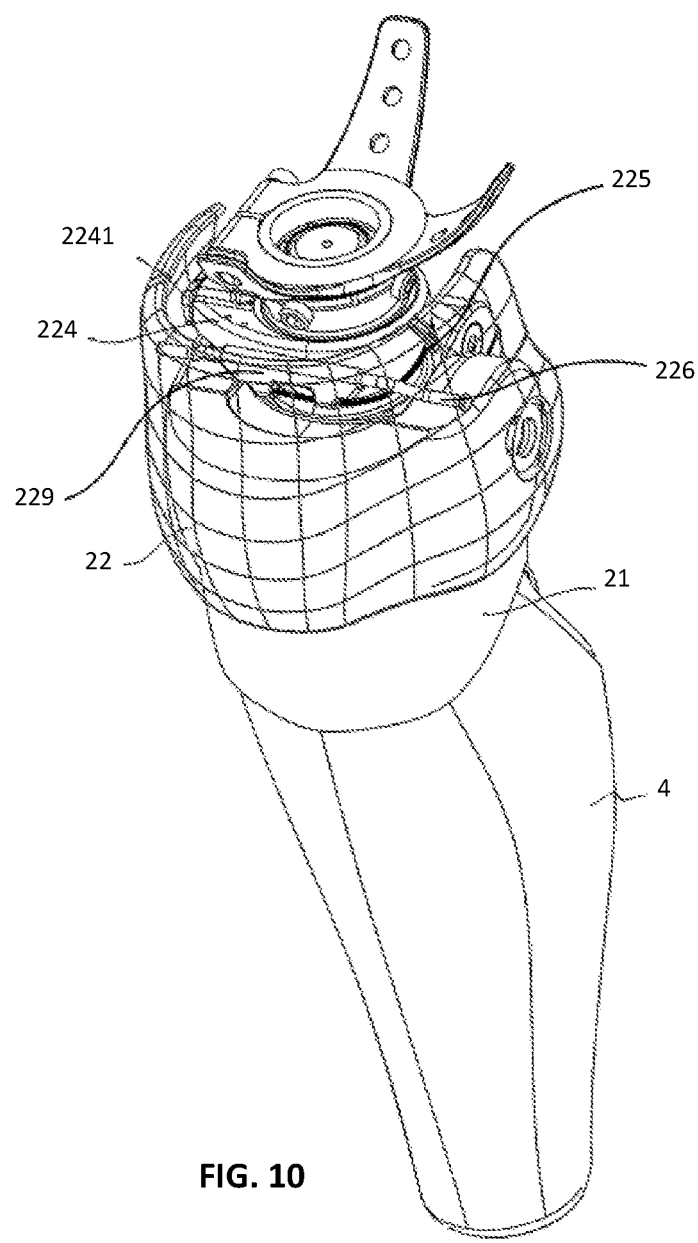
FIG. 10 is a detail view of the second frame part with a fastening elements and carrier.

FIG. 10 shows a detail view of the transitional area from the second frame part 22 to the prosthesis socket 6, not shown here. The second frame part 22 surrounds the connecting element between the prosthesis joint and the prosthesis socket, the connecting element is configured as a rotary adapter 224 and is attached to the prosthesis joint, at least partially. To the front, the rotary adapter is covered, as well as medially and laterally; but there exists an access or a possibility for actuating the former through or by the second frame part 22; to this end, the rotary adapter 224 is accessible from the outside for adjusting the orientation of the prosthesis socket 6 relative to the prosthesis knee joint or relative to the lower part 4. The second frame part 22 accommodates a fixation element 225, that is embodied here by way of a band, cable tie or the like, and a catcher 226, which is embodied by way of a stirrup, by means of which the rotary adapter 224 can be positioned and oriented relative to the second frame member 22. By the catcher 226 and the fixation element 225, the second frame part 22 is taken along with the upper part 3 during flexion of the prosthesis knee joint 2.

Figure 11:
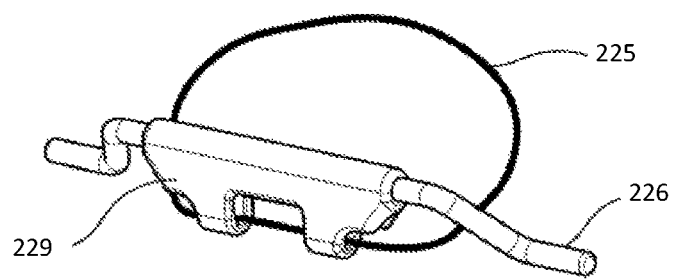
FIG. 11 is a detail view of the carrier and holder.

FIG. 11 shows in a single depiction the components by which the second frame part 22 according to FIG. 10 is held on the connecting element 11 and/or the rotary adapter 224. A fixation element 225 in the form of a band, a cable, a cable tie or a rope, which can also be elastic, is inserted in a receptacle inside a bracket 229 and fastened thereon. A catcher 226 in the form of a metallic stirrup is rotatably supported in the holder 229. The catcher 226 is mounted in the upper part 3, as shown in FIG. 10, in that the ends of the catcher 226 are inserted in corresponding recesses or guides within the second frame part 22. Using the fixation element 225, the holder 229, and thereby the catcher 226, is held closely to the connecting element 11 or the rotary adapter 224. To adjust it, the catcher 226 is rotated inside the upper part 22 until the catcher 226 comes to rest against the rotary adapter 224. This is achieved by providing the catcher 226 with an angular, crank-like shape, such that, by rotating the catcher 226 within the upper part 22, it is possible to displace the holder 229. When it is in the desired position, the catcher 226 can be fastened, for example, by means of gluing, screwing or clamping.

Figure 12:
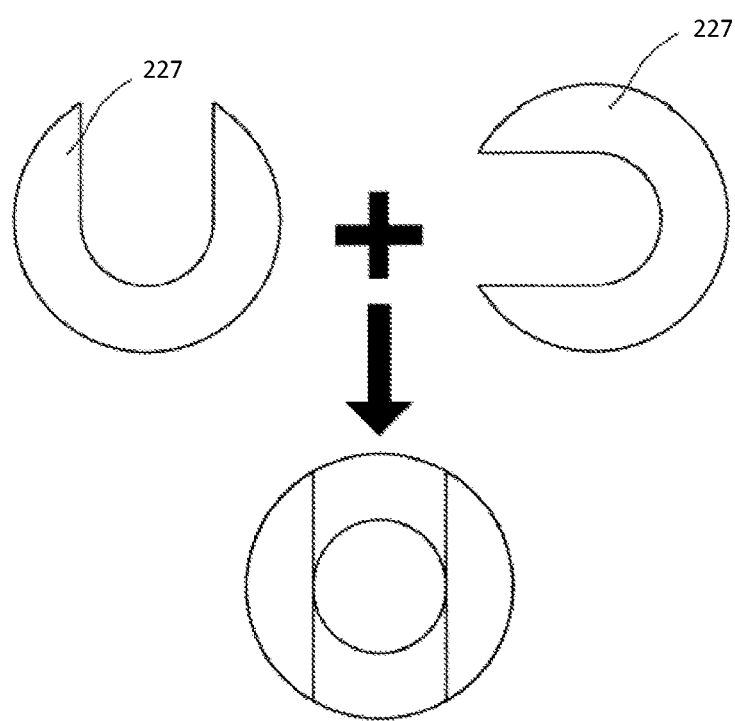
FIG. 12 is a separate view of spacer elements.

Another option for ensuring that the movement of the prosthesis knee joint is also performed by the second frame part 22 is given by the spacer elements 227 in FIG. 12. The spacer elements 227, as provided by way of two discs with oblong holes, can be disposed as surrounding the connecting element 11, which for example, can be in the form of a tube section, wherein the oblong holes or slots are rotated relative to each other in such a way that, once they have been installed, they are no longer displaceable along the respective oblong holes. The two discs 227 are complementary in their circumferences; this means, when they are placed one on top of the other, they form one fully closed disc.

Figure 13:
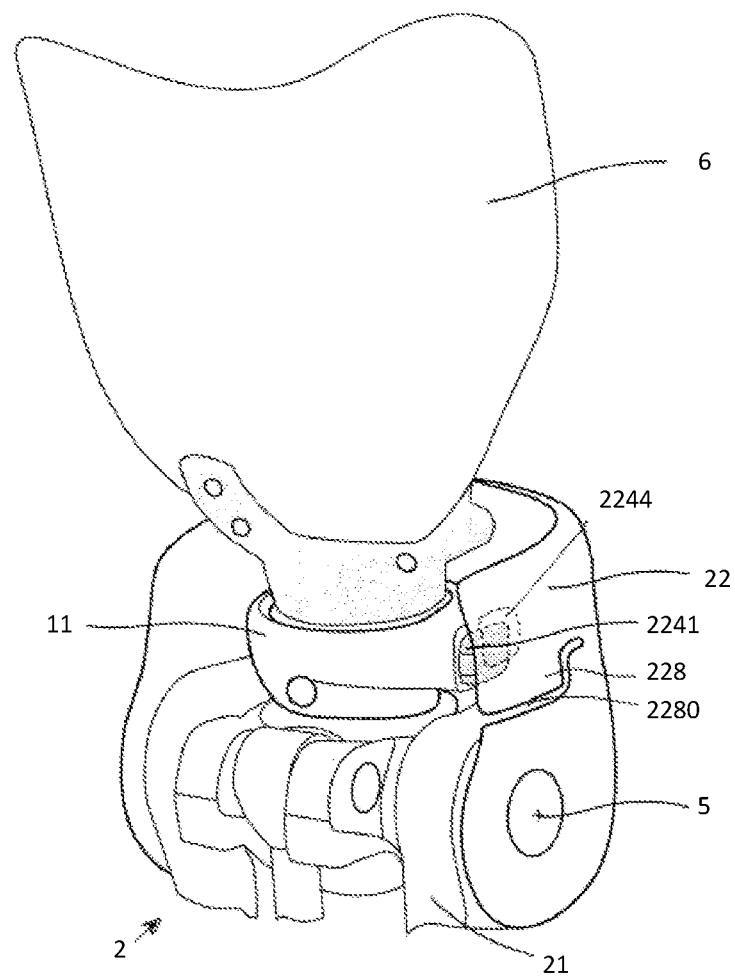
FIG. 13 is a perspective side view of a variant of the invention.

FIG. 13 depicts in a schematic representation the prosthesis knee joint 2 with a mounted first frame part 21 and a mounted second frame part 22 that is fastened to the upper part 3 so that when the upper part 3 is pivoted with the prosthesis socket 6 about the pivot axis 5, a relative displacement of the first frame part 21 relative to the second frame part 22 takes place. In the illustrated embodiment, the connecting element 11 that connects the upper part of the joint with the prosthesis socket 6 is configured as a rotary adapter having an actuating element 2241 that is located within the second frame part 22. The actuating element 2241 is laterally covered by a flexible section 228 of the second frame part 22 so that there is no direct access to the actuating element 2241. To actuate the actuating element 2241 that can trigger the upper part 3 and the prosthesis socket 6 to rotate relative to the lower part, for example, when sitting down, the flexible section 228 is displaced in the direction of the actuating element 2241. The flexibility of the section 228 is achieved by means of a slot 2280 that is configured within the second frame part 22, so that a displacement of the flexible section 228 is easily possible. The slot 2280 extends from a rear end of the second frame part 22 along a lateral wall, so that an inward bending of the flexible section 228 is easily possible.

If no flexible section 228 is to be provided or cannot be provided on the second frame part 22, as an alternative, a recess 2244 is provided that is formed in the area of the actuating element 2241 in the second frame part 22. The recess 2244 is hinted at in FIG. 13 by a dashed line. Instead of a recess, which is completely surrounded by the second frame part 22, it is possible to provide a cutout that originates from the back edge of the second frame part 22. FIG. 9 demonstrates the accessibility by means of a corresponding configuration of the first frame part 21.

| List of reference signs | |
| --- | --- |
| 1 | Prosthesis cosmetic element |
| 2 | Prosthesis knee joint |
| 3 | Upper part |
| 4 | Lower part |
| 5 | Pivot axis |
| 6 | Prosthesis socket |
| 7 | Molded part |
| 8 | |
| 9 | Fastening element |
| 10 | Prosthesis |
| 11 | Tube |
| 12 | Lower-leg tube |
| 13 | Prosthetic foot |
| 21 | First frame part |
| 211 | Head area |
| 212 | Strut |
| 213 | Strut |
| 214 | Slot |
| 22 | Second frame part |
| 221 | Head area |
| 222 | Bridging element |
| 223 | Bridging section |
| 224 | Rotary adapter |
| 225 | Fixation element |
| 226 | Catcher |
| 227 | Spacer element |
| 228 | Flexible section |
| 229 | Holder |
| 30 | Textile cover |
| 31 | Positive locking element |
| 32 | Force fitting locking element |
| 33 | Stiffener |
| 2211 | Extension |
| 2221 | Force fitting element |
| 2241 | Actuating element |
| 2244 | Cutout |

The invention claimed is:

1. A prosthesis cosmetic element for a prosthesis with a prosthesis joint which has an upper part and a lower part that is pivotably supported thereon about a swivel axis, the prosthesis cosmetic element comprising:
 a first frame part that includes at least one first securing member for fastening to the lower part;
 a second frame part that includes at least one second securing member for fastening to the upper part, the second frame part being pivotably supported relative to the first frame part;
 a rotational element disposed on the prosthesis joint, the rotational element being configured as a rotary adapter;
 an actuating element disposed on the rotational element, the actuating element being accessible from an outside of the prosthesis cosmetic element by one of the first and second frame parts or through one of the first and second frame parts.

2. The prosthesis cosmetic element according to claim 1, wherein the rotational element is at least partially surrounded by at least one of the first and second frame parts, wherein the rotational element can be actuated by going through the at least one of the first and second frame parts or by means of the at least one of the first and second frame parts.

3. The prosthesis cosmetic element according to claim 2, wherein the rotational element is fastened to the at least one of the first and second frame parts.

4. The prosthesis cosmetic element according to claim 2, wherein the rotational element is disposed on at least one of the second frame part and the upper part.

5. The prosthesis cosmetic element according to claim 1, wherein the first frame part includes a head area that is at least partially configured as ball-like or barrel-like and that is rotatably supported in the second frame part.

6. The prosthesis cosmetic element according to claim 5, wherein the second frame part includes a ball-like or partially barrel-like head area, the ball-like or partially barrel-like heads of the first and second frame parts overlap each another at least partially when the prosthesis joint is in an extended position, wherein one head area is received inside the other head area.

7. The prosthesis cosmetic element according to claim 6, wherein, in a flexed position of the prosthesis joint, the head areas surround the prosthesis joint at least partially, complementing each other.

8. The prosthesis cosmetic element according to claim 5, wherein the head area is configured as a separate component.

9. The prosthesis cosmetic element according to claim 1, wherein the first frame part is configured as shell-like or with struts extending in longitudinal extension of the lower part.

10. The prosthesis cosmetic element according to claim 1, wherein the first frame part proximally protrudes the pivot axis.

11. The prosthesis cosmetic element according to claim 1, wherein the second frame part includes at least one bridging element or a bridging section that extends in a direction of a prosthesis socket.

12. The prosthesis cosmetic element according to claim 11, wherein the bridging element or the bridging section can be fastened to the prosthesis socket.

13. The prosthesis cosmetic element according to claim 11, wherein the bridging element or the bridging section is rotatably supported relative to a head area of the first or second frame member or the prosthesis socket.

14. The prosthesis cosmetic element according to claim 1, wherein a receiving member in the form of a fastening element is disposed on the first frame part for attachment to a molded part having a contoured surface.

15. The prosthesis cosmetic element according to claim 1, wherein a textile cover covers the frame parts.

16. The prosthesis cosmetic element according to claim 15, wherein the textile cover includes positive locking elements or force fitting elements by means of which the cover can be fastened to at least one of the first and second frame parts, a prosthetic socket, a foam part, and a foot cover.

17. The prosthesis cosmetic element according to claim 15, wherein stiffeners are disposed in or on the textile cover.

18. The prosthesis cosmetic element according to claim 1, wherein at least one of the first and second frame parts includes fixation and spacer elements by which the at least one of the first and second frame parts is held on the prosthesis or spaced apart from the prosthesis.

19. The prosthesis cosmetic element according to claim 1, wherein the first frame part is produced from a dimensionally stable material.

20. A system consisting of a prosthesis cosmetic element according to claim 1, and the prosthesis having the prosthesis joint which has the upper part and the lower part mounted thereon in a pivotal manner about the swivel axis, wherein the rotational element is disposed on the prosthesis joint that has disposed thereon the actuating element that is accessible from the outside.

* * * * *